United States Patent [19]

Sanderson et al.

[11] Patent Number: 5,068,366

[45] Date of Patent: Nov. 26, 1991

[54] SIMULTANEOUS EPOXIDE AND CARBOXYLIC ACID MANUFACTURE BY CO-OXIDATION IN THE PRESENCE OF A COBALT CATALYST

[75] Inventors: John R. Sanderson, Leander; Edward T. Marquis, Austin, both of Tex.

[73] Assignee: Texaco Chemical Company, White Plains, N.Y.

[21] Appl. No.: 563,237

[22] Filed: Aug. 6, 1990

[51] Int. Cl.$^5$ ............... C07D 301/06; C07C 51/21
[52] U.S. Cl. ................... 549/533; 549/532; 562/531
[58] Field of Search ............ 549/533, 532; 562/531

[56] References Cited

U.S. PATENT DOCUMENTS

| | | | |
|---|---|---|---|
| 2,316,604 | 4/1943 | Loder et al. | 260/484 |
| 2,437,648 | 9/1943 | Milas | 260/617 |
| 3,076,842 | 2/1963 | Jason et al. | 260/533 |
| 3,173,933 | 3/1965 | Hay | 260/413 |
| 3,265,716 | 8/1966 | Dickey et al. | 260/348.5 |
| 3,347,763 | 10/1967 | Coffey et al. | 204/158 |
| 3,407,221 | 10/1968 | Lutz | 260/413 |
| 3,414,594 | 12/1968 | Dubeck et al. | 260/413 |
| 3,557,169 | 1/1971 | Robinson | 260/413 |
| 3,658,896 | 4/1972 | washecheck | 260/533 R |
| 3,716,562 | 2/1973 | Pregaglia et al. | 260/348.5 V |
| 3,974,207 | 8/1976 | Szelejewski et al. | 562/531 |
| 4,046,783 | 9/1977 | Cavitt | 260/348.33 |
| 4,098,817 | 7/1978 | Barone | 260/533 C |
| 4,220,800 | 9/1980 | Stapp | 560/246 |
| 4,256,650 | 3/1981 | Bljumberg et al. | 260/348.33 |
| 4,483,998 | 11/1984 | Sanderson et al. | 549/533 |

OTHER PUBLICATIONS

Kuledouska, M., *Chemical Abstracts*, 95:186591h, "Oxidation of Isobutyraldehyde", p. 596 (1981).

*Primary Examiner*—Richard L. Raymond
*Assistant Examiner*—Mork W. Russell
*Attorney, Agent, or Firm*—Jack H. Park; Kenneth R. Priem; David L. Mossman

[57] ABSTRACT

A process for the preparation of isobutylene oxide and isobutyric acid from isobutylene and isobutyraldehyde, respectively, by a co-oxidation process conducted in the presence of oxygen and a cobalt salt catalyst at a temperature of about 20° to about 180° C. is disclosed.

8 Claims, No Drawings

SIMULTANEOUS EPOXIDE AND CARBOXYLIC ACID MANUFACTURE BY CO-OXIDATION IN THE PRESENCE OF A COBALT CATALYST

BACKGROUND OF THE INVENTION

1. Field of the Invention

This invention relates to the preparation of an epoxide during the simultaneous oxidation of an aldehyde to the corresponding carboxylic acid. More particularly, this invention relates to the preparation of isobutylene oxide and isobutyric acid from isobutylene and isobutyraldehyde, respectively, by a co-oxidation process conducted in the presence of oxygen and in the presence of a homogeneous catalyst which is a soluble cobalt salt.

2. Prior Art

The preparation of ethylene oxide and propylene oxide by direct oxidation of the corresponding olefin in vapor phase in the presence of silver catalysts is known. Cooxidation processes are also well known in the art.

U.S. Pat. No. 3,265,716 discloses a process for the non-catalytic epoxidation of olefins such as cyclododecatriene, dicyclopentadiene, methyl-2-heptene, butene-2, octene-1, cyclooctene, with a secondary aliphatic aldehyde such as isobutyraldehyde, which is converted to the corresponding acid.

U.S. Pat. No. 4,256,650 discloses a process for preparing propylene oxide and acetic acid by oxidation of propylene and acetaldehyde in liquid phase at a temperature of from 70° to 100° C. under a pressure of 40 to 50 atm. and in the presence of a boride catalyst.

U.S. Pat. No. 3,716,562 discloses a liquid phase oxidation process in which in the first stage oxygen is reacted with an olefin and an aldehyde in the presence of an inert diluent while in the second stage the reaction is continued in the presence of a molybdenum catalyst and without oxygen addition.

U.S. Pat. No. 3,347,763 discloses a process for preparing an olefin oxide and a carboxylic acid in which a liquid mixture of an aldehyde and an olefinic compound containing at least four carbon atoms and having the double bond in a non-terminal position is contacted with oxygen at a temperature of 30° to 150° C. Catalysts such as copper, manganese, nickel or cobalt salts may also be used in this process.

U.S. Pat. No. 4,483,998 teaches a co-oxidation process for simultaneously producing an epoxide and a carboxylic acid in which an olefin and an aldehyde are contacted with oxygen in the presence of a catalyst containing copper, boron and silver.

U.S. Pat. No. 4,046,783 teaches a liquid phase process in which an olefin is converted to the corresponding oxirane by contacting the olefin with molecular oxygen in the presence of a suitable solvent and in the presence of a molybdenum-containing catalyst material.

U.S. Pat. No. 2,316,604 discloses a process for the controlled oxidation of normally liquid olefinic materials with molecular oxygen in the presence of a solvent which can be an organic acid and in the presence of catalyst such as cobalt acetate, cobalt permaganate, copper acetate, etc.

U.S. Pat. No. 3,658,896 discloses a process for the oxidation of an olefinic hydrocarbon which utilizes a catalytic system consisting of a minor amount of a ruthenium compound and a major amount of a peracid.

U.S. Pat. No. 3,557,169 teaches a process for preparing carboxylic acids in which alpha olefins are dimerized and the dimerized materials are then oxidized with molecular oxygen in the presence of a catalyst such as cobalt bromide.

U.S. Pat. No. 3,407,221 discloses a process for oxidizing olefins to carboxylic acids by intimately contacting the olefin in liquid phase with oxygen in the presence of a cerium salt-nitric acid mixture as catalyst.

U.S. Pat. No. 3,414,594 teaches a process for preparing carboxylic acids and ketones by oxidizing olefins in a lower alkanol reaction medium and in a second step, oxidizing the ozonized olefin with molecular oxygen in the presence of an aqueous mineral acid. The second step reaction can also be conducted, if desired, in the presence of a cobalt salt catalyst.

U.S. Pat. No. 3,173,933 discloses a process for preparing carbonyl containing alkyl compounds in which alkyl compounds are reacted with oxygen in the presence of a catalyst soluble in the reaction mixture and consisting essentially of cobalt, bromine and a carboxylic acid.

U.S. Pat. No. 3,076,842 teaches a process by which an alkene-1, such as 1-octene, is oxidized with molecular oxygen to form an aliphatic, monocarboxylic acid product. The reaction is conducted at a temperature of about 50° to 200° C. and in the presence of a catalyst system comprising bromine and a heavy metal oxidation catalyst such as cobalt, nickel, iron supplied in elemental form, as the oxide or hydroxide or as a salt of the metal.

U.S. Pat. No. 2,437,648 discloses a process for the catalytic oxidation of unsaturated organic compounds such as olefins to yield products such as glycols, aldehydes, ketones and organic acids. The reaction is conducted in the presence of an inert, organic solvent, hydrogen peroxide and a small amount of a catalytically active oxide of a metal such as osmium, ruthenium, vanadium, etc.

U.S. Pat. No. 4,220,800 teaches a process for the conversion of olefinic carbon-carbon double bonds to vicinal diester groups by oxidation of the olefin compound which can be, for example, propylene, in the presence of a boron-containing catalyst and a carboxylic acid, carboxylic acid anhydride or mixtures thereof.

U.S. Pat. No. 4,098,817 discloses a process in which cycloaliphatic compounds are reacted in an organic ester solvent with molecular oxygen in the presence of a catalytic amount of, for example, cobalt acetylacetonate to form dibasic acids.

SUMMARY OF THE INVENTION

This invention is an oxidation process for simultaneously producing isobutylene oxide and isobutyric acid comprising contacting a mixture of isobutylene and isobutyraldehyde in a liquid phase reaction with oxygen in the presence of a soluble cobalt salt catalyst.

DESCRIPTION OF THE PREFERRED EMBODIMENTS

In this process isobutyric acid and isobutylene oxide are produced simultaneously. Isobutyric acid is useful for manufacturing esters for solvents, flavors and perfume bases, as a disinfecting agent and as a tanning agent, etc. A wide variety of products such as urethane polyols, surfactants and detergents, fumigants, synthetic lubricants, etc. can be prepared with isobutylene oxide.

Preferably, in carrying out the process of this invention, a suitable reaction vessel such as an autoclave equipped with a mechanical stirrer is charged with isobutyraldehyde, the cobalt catalyst and a solvent. The reaction vessel is then sealed and isobutylene pressured in after which the reaction mixture is heated to the reaction temperature with stirring and oxygen is added in small incremental amounts. The reaction is continued until the desired degree of epoxidation of the olefin is attained.

The products of this invention can be recovered from the reaction mixture by known methods such as distillation, extraction, recrystallization, chromatography, and the like.

In this process the proportion of isobutylene to isobutyraldehyde should range on a 2 molar basis from about 0.1:4.0 to 4.0:0.1 and preferably from about 2.5:1.0 to 0.75:1.0.

Catalysts useful in the process of this invention include soluble cobalt salts such as stearates, naphthenates, benzoates, oleates, acetylacetonates, acetoacetates, etc. Mixtures of these same soluble cobalt salts can be utilized, if desired. Only a catalytically effective amount of the soluble cobalt salt catalyst is required.

The process of this invention can be conducted using molecular oxygen in the pure form or an oxygen-containing gas, such as air, may be utilized.

Solvents useful in this process must be inert with respect to the oxidation reaction and include non-polar aromatic organic solvents as exemplified by halobenzenes, alkylbenzenes, etc. Preferred solvents are chlorobenzene and dichlorobenzene.

The reaction temperature will range from about 20° C. to about 180° C. with the preferred range being about 50° C. to about 100° C. The reaction pressure employed can be varied over a wide range and generally will be from about 1 to about 70 atmospheres or greater with the preferred pressure ranging from about 20 to about 40 atmospheres.

The reaction time required will depend on the ratio of isobutylene to isobutyraldehyde, the reaction temperature, the reaction pressure, the particular cobalt salt used, and the various other factors which may enter into the reaction. In general the reaction time will vary from about 1 to about 20 hours or more with the preferred reaction time being from about 1 to about 10 hours.

The preparation of isobutylene oxide and isobutyric acid with the process of this invention is described in the following examples which are not to be construed to be limiting in any way.

EXAMPLE 1 AND COMPARATIVE EXAMPLES 2, 3, AND 4

In Example 1, which represents the process of this invention, isobutylene was reacted with isobutyraldehyde in the presence of oxygen and cobalt acetylacetonate catalyst. In Comparative Examples 2, 3 and 4, isobutylene was reacted with butyraldehyde, heptaldehyde and benzaldehyde, respectively.

In all of these examples a 300 cc stainless steel autoclave was charged with chlorobenzene solvent, aldehyde and catalyst in powder form. The autoclave was sealed and isobutylene pressured in. The reaction mixture was then heated to 80° C. with stirring and oxygen added in 1-2 g increments. At the end of 4.0 hours, the reaction mixture was cooled to ambient temperature, vented slowly and the liquid contents poured into a bottle. The reactor effluent was analyzed by gas chromatography to determine the percent yield of isobutylene oxide, the carboxylic acid and heavy unknown compounds. Details of these examples are shown in Table I below.

TABLE I

REACTION OF ISOBUTYLENE WITH ALDEHYDES IN THE PRESENCE OF CHLOROBENZENE AND COBALT ACETYLACETONATE

| | Reactants | | | | | | Products, | | |
|---|---|---|---|---|---|---|---|---|---|
| | Iso- | | | | | | Catalyst | A % Solvent-Free Basis$^a$ | | |
| | butylene | | | Oxygen | Time | Temp. | Weight | Isobutylene | | |
| Example | (g) | Aldehyde | g | (g) | (Hr) | (°C.) | (g) | Oxide | Acid | Heavies |
| 1 | 30.5 | Isobutyraldehyde | 36.1 | 16.0 | 4.0 | 80 | 0.01 | 20.3 | 12.5 | 5.7 b |
| 2 | 29.1 | Butyraldehyde | 36.1 | 16.0 | 4.0 | 80 | 0.01 | 17.7 | 20.7 | 15.4 b |
| 3 | 28.1 | Heptaldehyde | 57.1 | 16.0 | 4.0 | 80 | 0.01 | 7.0 | 15.1 | 9.6 c |
| 4 | 28.4 | Benzaldehyde | 53.1 | 15.0 | 4.0 | 80 | 0.01 | 12.8 | n.d. | >18 c |

$^a$Products determined by gas chromatographic analysis.
$^b$Heavies = >12 min retention time
$^c$Heavies = >20 min retention time It is shown in Example 1 that with the process of this invention a higher yield of isobutylene oxide was obtained with less formation of heavy compounds when isobutylene was co-oxidized with isobutyraldehyde than was obtained when other aldehydes were co-oxidized with isobutylene.

What is claimed is:

1. A co-oxidation process for simultaneously producing isobutylene oxide and isobutyric acid comprising:
    contacting a mixture of isobutylene and isobutyraldehyde in the liquid phase with oxygen in the presence of a soluble cobalt salt catalyst and in the presence of an organic, inert solvent.

2. The process of claim 1 wherein the proportion of isobutylene to isobutyraldehyde ranges from 0.1:4.0 to 4.0:0.1.

3. The process of claim 1 wherein the reaction is conducted at a temperature between about 20° and about 180° C.

4. The process of claim 1 wherein the reaction is conducted at a pressure ranging from about 1 to about 70 atmospheres.

5. The process of claim 1 wherein the said soluble cobalt salt catalyst is selected from the group consisting of cobalt acetylacetonate, naphthenate, acetate, octoate, heptanoate, and nitrate.

6. The process of claim 1 wherein the said soluble cobalt salt catalyst is cobalt acetylacetonate.

7. The process of claim 1 wherein the said organic, inert solvent is chlorobenzene.

8. A co-oxidation process for simultaneously producing isobutylene oxide and isobutyric acid comprising:
    contacting a mixture of isobutylene and isobutyraldehyde in liquid phase with oxygen in the presence of cobalt acetylacetonate, and in the presence of chlorobenzene and at a temperature of from about 20° and about 180° C.

* * * * *